United States Patent [19]

Kolb et al.

[11] Patent Number: 5,055,592

[45] Date of Patent: Oct. 8, 1991

[54] NOVEL PROCESS AND INTERMEDIATES

[75] Inventors: Michael Kolb, Truchtersheim; Luc Van Hijfte, Marlenheim, both of France

[73] Assignee: Merrell Dow Pharmaceuticals, Cincinnati, Ohio

[21] Appl. No.: 474,317

[22] Filed: Jan. 30, 1990

Related U.S. Application Data

[62] Division of Ser. No. 302,508, Nov. 26, 1989, abandoned.

[30] Foreign Application Priority Data

Jan. 28, 1988 [EP] European Pat. Off. ........ 88400199.1

[51] Int. Cl.$^5$ .......................................... C07C 177/00
[52] U.S. Cl. .................................... 549/206; 549/416; 549/420; 549/423; 556/87; 556/112; 556/436; 556/446; 560/121; 562/503
[58] Field of Search ........................ 560/121; 562/503; 549/206, 420, 423, 416; 556/112, 87, 436, 446

[56] References Cited

U.S. PATENT DOCUMENTS 4,841,091  6/1989  Tanaka ................................ 558/441

FOREIGN PATENT DOCUMENTS 79733  5/1983  European Pat. Off. ............ 560/121

OTHER PUBLICATIONS

Noyori, Angew Chemie Int Ed. Eng 23 847–876 (1984) "Prostaglandin Synthesis by Three–Component Coupling".

Primary Examiner—Robert Gerstl
Attorney, Agent, or Firm—J. Michael Dixon

[57] ABSTRACT

This invention relates to the novel processes for the preparation of a 16-methoxy-16-methyl prostaglandin $E_1$ derivative and to the novel intermediates useful therefor.

5 Claims, No Drawings

NOVEL PROCESS AND INTERMEDIATES

This is a divisional of application Ser. No. 07/302,508, filed Jan. 26, 1989, now abandoned.

This invention relates to the novel processes for the preparation of a 16-methoxy-16-methyl prostaglandin E₁ derivative and to the novel intermediate useful therefor.

More specifically this invention relates to the novel enantioselective synthesis for the preparation of the methyl ester of (8R11R, 12R,15R,16R)11,15-dihydroxy-16-methyl-16-methoxy-9oxo-prost-13-en-1-oic acid, a prostaglandin-type gastro-protective agent previously described in U.S. Pat. No. 4,547,521 having the structural formula

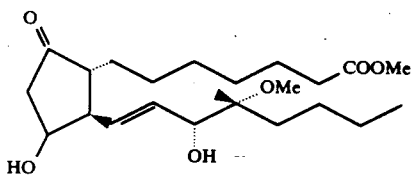

From an examination of the depicted structure of the compound of Formula I it is obvious that the compound has five stereogenic centers. It is also known that the biological profile of this compound is dependent upon the precise orientation of each moiety at each of these stereogenic centers. Modification at any one center will adversely affect the gastroprotective properties of the resulting compound. Because of this criticality it is extremely important to have a synthesis which is not only sensitive to this enantioselective need but one which is also commercially feasible. Unfortunately, while the heretofore known processes took into consideration the enantiomeric specificities, they did not facilitate the preparation of the compound of Formula I in a commercially viable manner. It is therefore an object of this invention to provide the necessary intermediates and syntheses to produce the compound of Formula I in its specific enantiomeric configuration and to facilitate its production in commercial quantities at a reasonable cost within a reasonable time. This invention, therefore, relates to the intermediates and processes which will accomplish these objectives.

In one of its process aspects, this invention provides a 1,4-Michael addition reaction using either a three-component or a two-component Michael reaction system, both of which lead to the enantiomerically pure compound of formula I. A general overview of these 1,4 Michael addition reactions may be depicted by the following reaction Scheme.

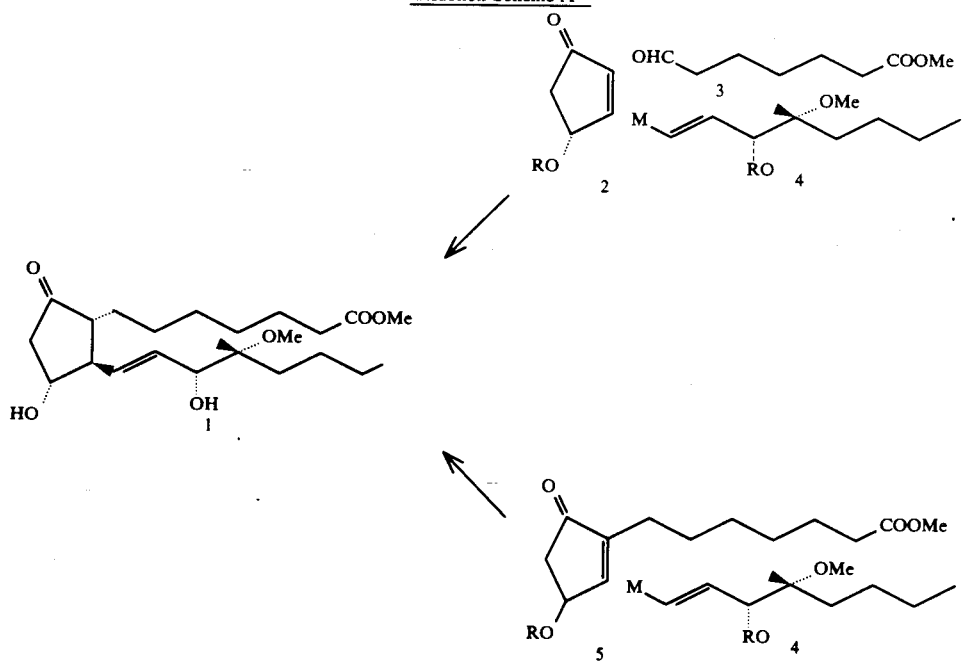

wherein M, in its initial form, is a (Bu)₃Sn-moiety ((bu) being n-butyl), but which moiety is modified to another reactive metallo moiety in the various steps of the reactions, R is a hydroxy protecting group and Me is methyl.

In its product aspects, this invention relates to the necessary enantiomerically pure reactants for the foregoing reactions, and, in another process aspect of this invention, to the processes for their preparation. These key enantiomerically pure intermediates are compounds of the formula

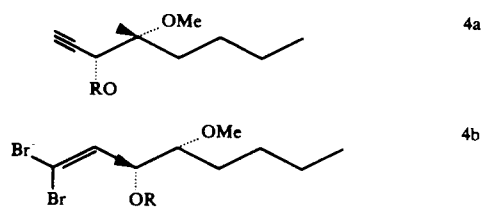

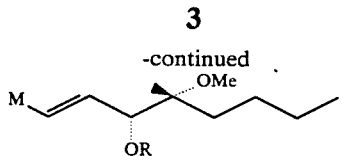

wherein M is either (Bu)₃Sn, lithium, or reactive copper either as a lower or higher order mixed organic cuprate complex (preferably for the two component reaction) or a reactive cupric moiety (preferably for use in the three component reactions), and R is a hydroxy protecting group preferably THP (tetrahydropyranyl) or TBS (t-butyldimethylsilyl). Handy references to the higher or lower order cuprate complex moieties useful for the 1,4-additions of this invention are Tetrahedron Letters, Vol. 28, No. 9, pp. 945–948 (1987) and the review article by B.H. Lipshutz in Synthesis, April 1987, pp. 325–341.

In the preparation of the desired enantiomeric form of the side chains of Formula 4, the known compound (2R, 3S) 2,3-epoxy-3,7-dimethyl-6-octene-l-ol (see JACS, 1980, 102, 5974) is conveniently used as a starting material and is converted to a benzyl ether under standard etherification procedures with benzyl bromide in the presence of potassium t-butoxide using lower temperatures (below 10° C.). Of course the alcohol may be converted to other ethers but care should be utilized to ensure functional equivalence in its selective removal relative to t.butyl dimethylsilyl, tetrahydropyranyl and alkyl ethers. Following etherification, the epoxide is opened by acid alcoholysis by contacting it with methanol at room temperature in an acidic environment; preferably Dowex 50, an acidic resin, is used to supply the acidic environment. The opening of the opoxide is effected with inversion at the 3-position and without change at the 2-position to yield the desired enantiomerically pure (2R, 3R)l-benzyloxy-3-methoxy-3,7-dimethyl-6-octene-2-ol. This compound is subjected to ozonization by treatment with ozone at about −50° C. to −80° C. (preferably -60° C.), the product subjected to a Wittig reaction with methyltriphenyl phosphonium bromide in the presence of potassium t-butoxide in THF according to standard techniques (room temperature - anhydrous conditions) to obtain the correct olefin (2R, 3R)l-benzyloxy-3-methoxy-3-methyl-6-heptene-2-ol.

This intermediate may be subjected to alternative syntheses (depending upon the 2-OH protecting group) to produce a resulting 2-OR-3-methoxy-3-methyl-6-heptene; R being THP or TBS (i.e. tetrahydropyranyl or t.butyl dimethylsilyl, respectively). These reactions are effected under standard conditions. The resulting olefin is chemically reduced, preferably by catalytic hydrogenation, which also effects debenzylation and the resulting alcohol oxidized to its corresponding aldehyde, preferably using the Swern oxidation techniques (e.g. with dimethylsulfoxide in an anhydrous medium under a nitrogen atmosphere and in the presence of oxalyl chloride), the reaction being completed by the addition of a base, e.g. triethylamine. The so-obtained aldehyde is subjected to dibromomethylenation (using tetrabromomethane and triphenylphenylphosphine) and the resulting 1,1-dibromo-4-methoxy-4-methyl-3-OR-l-octene (4b) is subjected to a debrominative rearrangement via a modified Fritsch-Buttenberg-Wiechell reaction to produce the desired acetylenic compound (4a). The rearrangement preferably utilizes either iodine-activated magnesium turnings or n-butyl lithium according to standard techniques. The so-obtained (3R, 4R)-3-OR-4-methoxy-4-methyl-l-octyne (R being THP or TBS) compounds (4a) are converted to their respective 1-tributylstannyl derivatives (4c) by standard procedures which involve reaction of the compounds of Formula 4a by heating with tri-n-butylstannyl hydride at about 80° C. to 150° C. (preferably 130° C.) in the presence of azoisobutyronitrile (AIBN). Once purified these tin olefins are ready for use in the preparation of the desired compound of Formula I using a three component condensation reaction or a two component Michael addition approach. The foregoing reactions for the preparation of the enantiomerically pure side chain may be schematically represented by the following reaction scheme.

Reaction Scheme B:

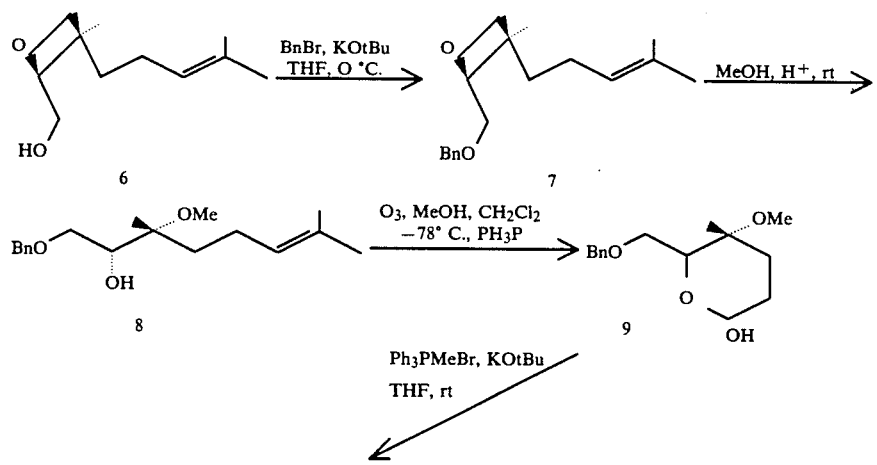

-continued

Reaction Scheme B:

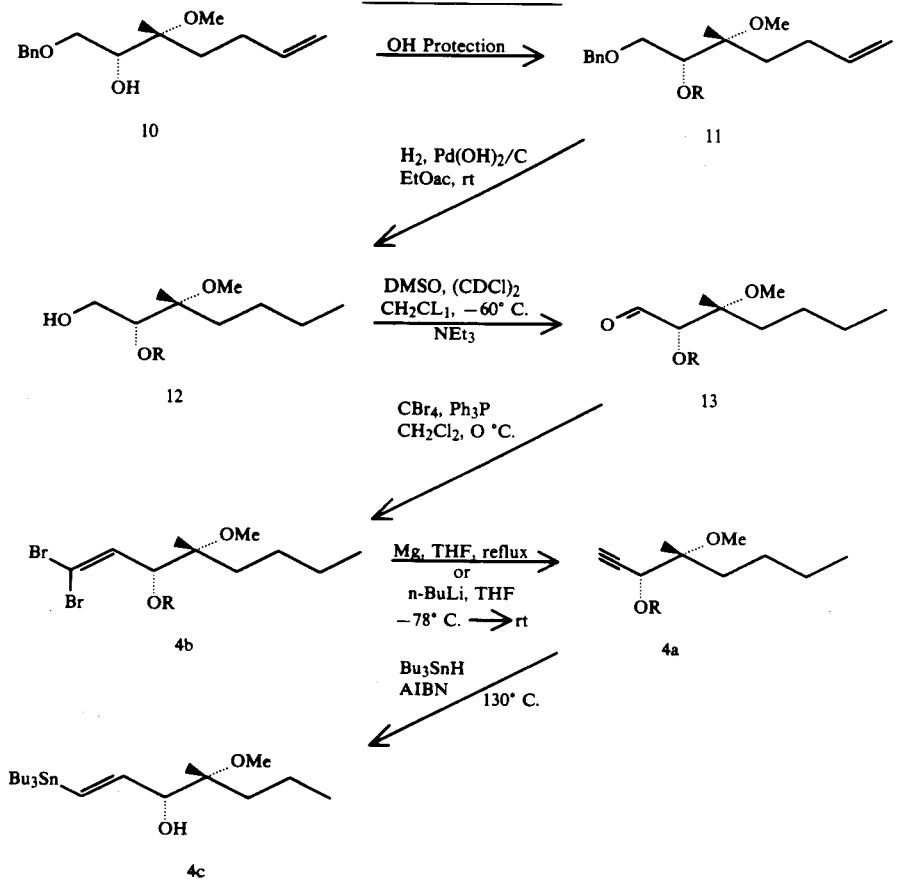

In essence, the three component condensation reaction involves in situ the formation of a 1-lithio derivative of a compound of Formula 4c (wherein M is lithium) which derivative reacts with cupric iodide and n-tributyl phosphine to form a reactive cupric moiety which reacts with the THP or TBS hydroxy-protected 4(R) hydroxy cyclopentenone (2), whereafter the formed enolate anion is trapped, in situ, with the aldehyde 3- to form an alcohol (14) which is subjected to sequential dehydration, 1,4-reduction and deprotection reactions to form the desired compound of Formula 1. These reactions are depicted in the following reaction scheme.

Reaction Scheme C:

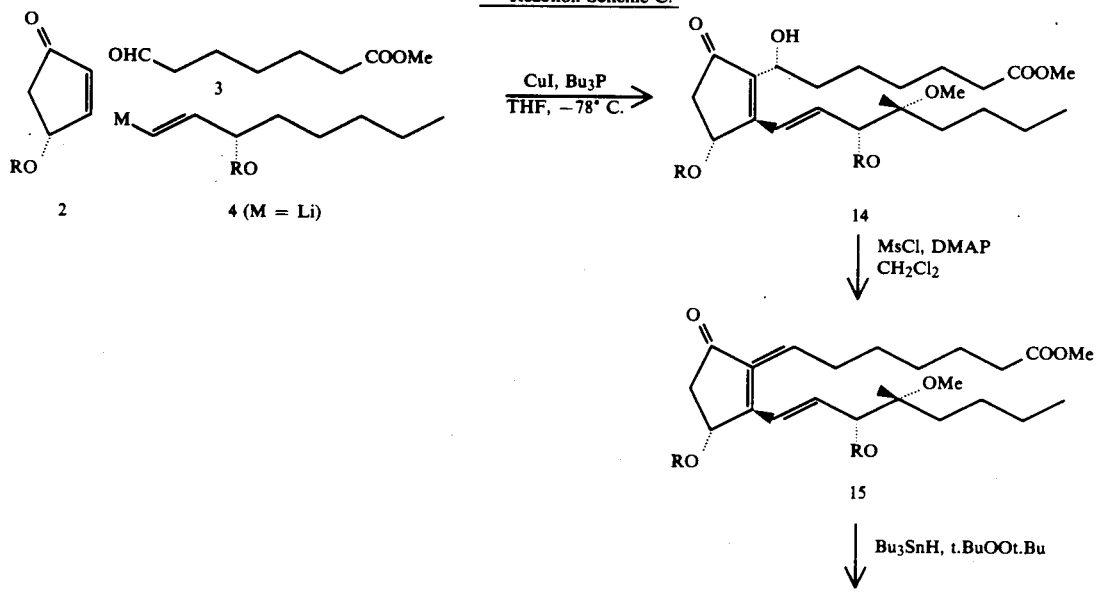

-continued
Reaction Scheme C:

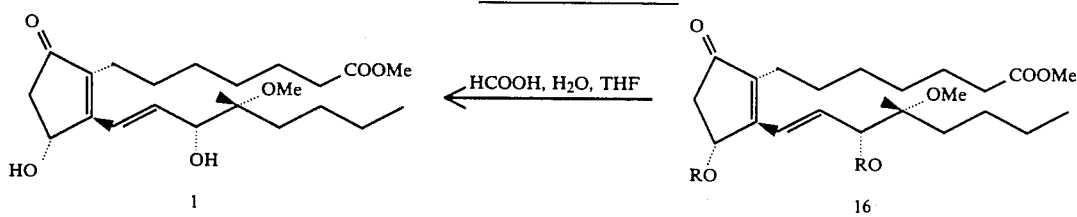

In effecting the reactions of the foregoing reaction scheme, the insitu formation of the copper complex is accomplished by reacting the lithio derivatives (4) with cupric iodide and tri-butyl phosphine at temperatures of about −60° C. to −20° C., preferably -35° C. The mixture containing the resulting complex is cooled to about −78° C. before adding the protected cyclopentenone (2) and the resulting mixture is allowed to warm slightly (about −40° C.) to react to form an enolate. The mixture is re-cooled to about −78° C. and the third component (i.e. the aldehyde of Formula 3) is added to the mixture containing the enolate and the resulting mixture is allowed to warm to room temperature to produce the expected compounds of Formula 14. The foregoing condensations are conducted under an inert atmosphere, preferably using nitrogen or argon, in a nonpolar solvent (e.g. THF) under anhydrous conditions. Following the condensation, the dehydration is effected using mesyl chloride (MsCl) and dimethylaminopyridine (DMAP) in an inert solvent (preferably CH$_2$Cl$_2$) at room temperature. The so-obtained product is generally purified using silica gel chromatogrpahy techniques prior to the 1,4-reduction. In effecting the reduction, tri-butylstannyl hydride is effectively utilized and the resulting reduced compounds (16) are deprotected according to standard acidic hydrolysis or acidic alcoholysis techniques.

The two components 1,4-addition may be schematically represented by the following scheme.

Reaction Scheme D

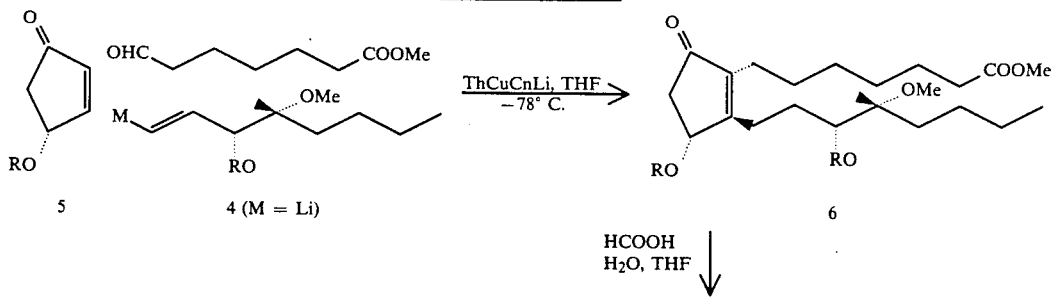

The enantiomerically pure hydroxy-cyclopentenone 5 (wherein R is H and Me is methyl) is a commercially available product.

The 4-hydroxy-protected cyclopenten-2-one reactant of Reaction Scheme A (i.e., compound 2) is readily obtained by reacting cyclopentadiene with singlet oxygen in an alcohol (MeOH) and thiourea to obtain a cis-diol which is converted to its diacetate. One acetate function is selectively removed using an enzymatic hydrolysis with pig liver esterase (PLE) and, following recrystallization of the monoacetate the hydroxyl function is protected with TBS or THP. (Formation of the TBS ether is effected with t.butyl dimethylsilyl chloride in DMF, in the presence of imidazole at room temperature, and formation of the THP ether is effected with dihydropyran and pyridinium p-toluenesulfonate in an anhydrous solvent (CH$_2$Cl$_2$) under a nitrogen atmosphere). Following etherification, the ether derivative is subjected to selective hydrolysis (to remove the acetate) and the resulting product oxidized to yield the desired reactant 2. These reactions are summarized in the following reaction scheme.

Reaction Scheme E:

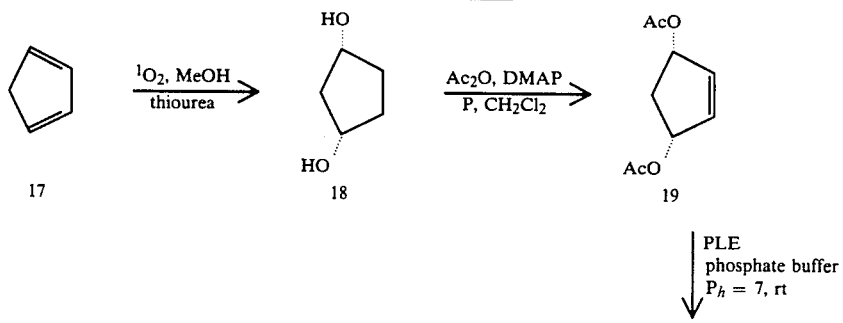

Reaction Scheme E:

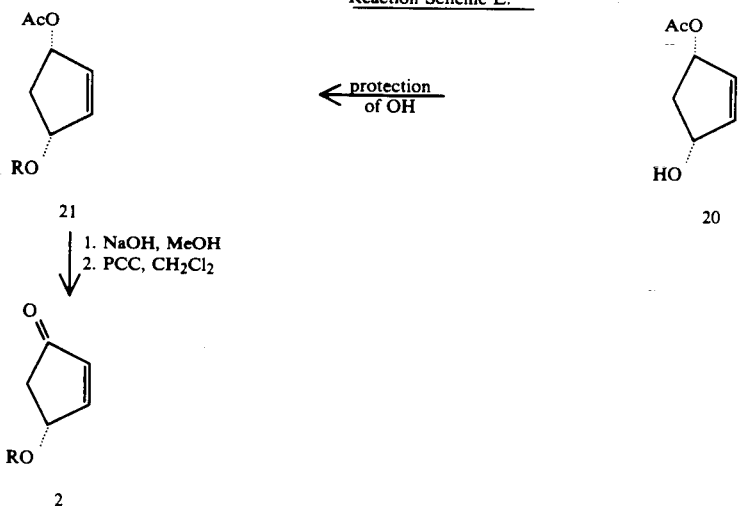

wherein R is TBS or THP, PCC is pyridinium chlorochromate, DMAP is dimethylaminopyridine, Py is pyridine.

The foregoing reactions are further detailed by the following examples.

PREPARATION OF INTERMEDIATES

Example I

PREPARATION OF (3R,4R)3-t.BUTYL DIMETHYLSILYLOXY-4-METHOXY-4-METHYL-1-OCTYNE (4a)

Step A

(2R,3S)2,3-EPOXY-3,7-DIMETHYL-6-OCTENE-1-OL (6)

A 2 liter 3-necked flask is fitted with an overhead mechanical stirrer, a thermometer and a pressure equalizing additional funnel. Activated crushed 3A molecular sieves (15 g) are brought in the flask, and the set up is dried under vacuum while heating with the heat gun. The flask is purged with nitrogen. Dry dichloromethane (dried over activated mol sieves, 600 ml) is introduced and the mixture is cooled to $-15°$ C., utilizing a glycol/water: 4/6 mixture-dry ice cooling bath or a cryocool apparatus. D-(-)-Diethyltartrate (77.8 mmol, 13.3 ml), titanium tetraisopropylate (58.3 mmol, 17.3 ml) and t.butyl-hydroperoxide (583 mmol, 194 ml of a 3 M solution in toluene (Fluka) are added sequentially. The mixture is agitated for 20 minutes at $-15°$ C., and the temperature is lowered to $-25°$ C. Nerol (389 mmol, 60 g, 68.5 ml) is added over a period of 30 min with vigorous stirring. The reaction mixture is kept for 3 h at $-20°$ C. The cooling bath is removed, and the reaction mixture is allowed to warm to $0°$ C., at which moment water (340 ml) is added in one portion. After 15 min (internal temperature 17° C.), a solution of 30% NaOH in concentrated NaCl (72 ml, prepared by adding 5 g NaCl to a solution of 30 g NaOH in 90 ml of water). A sudden phase separation occurs, and the stirring is stopped immediately. The mixture is transferred to an extraction funnel and the $CH_2Cl_2$ layer is removed. The water layer is extracted with $CH_2Cl_2$ (3×300 ml). Emulsions are broken by adding 15 ml of MeOH, while gentle stirring with a glass bar. The combined organic layers are washed with brine, dried over $MgSO_4$ and concentrated in vacuo. Distillation (95°-97° C., 0.03 mmHg) affords 65.7 g (99%) of the desired epoxide $[\alpha]_D = +15.4°$ (C =3.3, $CHCl_3$).

Step B

(2R,3S)2,3-EPOXY-3,7-DIMETHYL-6-OCTENE-1-OL, BENZYL ETHER (7)

To a solution of the alcohol 6- (386 mmol, 65.7 g) in dry THF (400 ml), cooled in an ice-salt bath, is added benzyl bromide (463 mmol, 72.6 g), followed by the portionwise addition of potassium t.butoxide (463 mmol, 52 g), so that the temperature is kept below 10° C. The cooling bath is removed and the mixture is stirred overnight at room temperature. $NEt_3$ (15 l) is added and the mixture is stirred for an additional 24 h. THF is then evaporated and the residue is extracted with ethyl ether/water. The organic phase is dried over sodium sulfate, evaporated, to afford 3 as an oil. The crude ether is used without further purification in the next step.

Step C

(2R,3R)-1-BENZYLOXY-3-METHOXY-3,7-DIMETHYL-6-OCTENE-2-OL (8)

To a solution of the crude ether 7 (120 g) in methyl alcohol (1 L) is added prewashed Dowex 50 (6 g). The mixture is stirred overnight at room temperature. TLC (petroleum ether/ethyl acetate: 80/20) indicates an uncomplete reaction. Dowex 50 is added, the reaction is stirred for an additional 24 h at room temperature. Dowex 50 is filtered and washed with dichloromethane. The organic solution, after addition of potassium carbonate (1 g), is kept without further purification for the next step.

Step D

(2R,3R)2-BENZYLOMETHYL-6-HYDROXY-3-METHOXY-3-METHYLTETRAHYDROPYRAN (9)

A 2 L 3-necked flask, fitted with a thermometer and a gas bubbler, is loaded with a solution of 8- (0.098 mol) in 750 ml of a $MeOH/CH_2Cl_2$: 1/1 mixture. The acid-free reaction mixture is cooled in a dry ice-acetone bath (internal temperature approximately $-60°$ C.), and ozone is bubbled through the solution. The mixture is stirred with a magnetic stirrer. After approximately 1½ h, the solution turns blue, and the ozone bubbling is stopped.

A few drops of dimethylsulfide are added so that the blue color disappears (reduction of excess ozone). Triphenylphosphine (0.1 mol, 26.3 g) is added in one portion, and the cooling bath is removed. The mixture is allowed to warm slowly to room temperature and the stirring is continued for 1 h. The solvent is removed on the rotary evaporator. Finally, traces of methanol are removed by addition and evaoporation of toluene (2 times with 100 ml). The residue is taken up in 100 ml of anhydrous THF, and the product 9 is used as such in the next reaction.

Step E

(2R,3R)1-BENZYLOXY-3-METHOXY-3-METHYL-6-HEPTENE-2-OL (10)

A dry 4 liter 3-necked flask, fitted with a thermometer, mechanical stirrer and addition funnel, is loaded with $Ph_3PCH_3Br$ (1.5 eq., 0.588 mol, 210 g), dried overnight at 80° C. under vacuum. The system is purged with nitrogen. Anhydrous THF (600 ml) is introduced, the reaction mixture is cooled in a crushed ice-water bath, and KOt.Bu (2 eq., 0.784 mol, 88 g) is added (the mixing is exothermic) to give a bright yellow solution. The cool bath is remove, and 9 of Step D is added dropwise over ½ h via an addition funnel with THF (150 ml). The mixture is stirred for 3 h at room temperature. The reaction is cooled in an ice-water bath, and 800 ml of a saturated $NH_4Cl$ solution is added. The mixture is extracted with ethyl acetate, the water layer is removed and extracted once with ethyl acetate. The organic phase is washed with water and brine. After drying over sodium sulfate, the solvent is removed on the rotary evaporator. The residue is taken in petroleum ether (scratching and mixing precipitate the $Ph_3P=O$). Filtration of the triphenylphosphine oxide, washing 3 times with petroleum ether, followed by evaporation of the organic phase, affords the desired alkene as an oil. The alkene 10 is purified by filtration through a short path of silicagel, eluting successively with 95/5 petroleum ether/ethyl acetate (to rinse off the $Ph_3P$) followed by elution with petroleum ether/ethyl acetate: 70/30 yields the reaction product 10 as a yellow oil.

Step F

(2R,3R)1-BENZYLOXY-2-t.BUTYL DIMETHYLSILYLOXY-3-METHOXY-3-METHYL-6-HEPTENE (11a)

To a solution of 10 (51.37 g, 194.3 mmol) in anhydrous DMF (500 ml) at room temperature under nitrogen, is added imidazole (2 eq, 26.44 g, 388.5 mmol) followed by t. butyl dimethylsilyl chloride (1.5 eq, 44 g, 291.5 mmol). The mixture is stirred for 2 days. DMF is removedd under reduced pressure, water (1 L) is added, and the mxiture is extracted with ethyl ether (2×500 ml). The combined organic fraction is washed with 1 N HCl, then saturated $NaHCO_3$ and brine. After drying over sodium sulfate, the solution is evaporated. The residue is filtered through a short path of silicagel, first eluting with petroleum ether to remove the siloxanes, then with petroleum ether/ethyl acetate: 90/10 to collect the silyl ether 11a (60.6 g, 82.3%).

Step G

(2R,3R)2-t.BUTYL DIMETHYLSILYLOXY-3-METHOXY-3-METHYL-1HEPTANOL (12a)

A solution of 11a (60 g, 158. 6 mmol) and $Pd(OH)_2$ on carbon (6 g) in ethyl acetate (600 ml) is hydrogenated at 1 atmosphere overnight. The reaction can be monitored by TLC. The catalyst is removed by filtration through a short path of celite. The filtrate is evaporated and the acid-sensitive alcohol 12 is filtered through a short path of silica gel, eluting with petroluem ether/ethyl acetate: 80/20 to afford the desired product 12a of this step as an oil.

Step H

(2R,3R)2-t.BUTYL DIMETHYLSILYLOXY-3-METHOXY-3-METHYL-HEPTAN-ALDEHYDE (13a)

A solution of 12a (43 g, 148 mmol) and DMSO (2 eq, 21.5 ml) in dry dichloromethane (750 ml) under nitrogen is cooled in a dry ice-acetone bath. Oxalyl chloride (1.3 eq, 16.12 ml) is added dropwise. During the addition, gas evolution occurs. The mixture is stirred for 15 min, and triethylamine (4.5 eq, 88 ml) is added in one portion (a white solid precipitates). The cooling bath is removed to allow the mixture to warm to room temperature. Ethyl ether (2 L) is added, and water (4 L) to dissolve the precipitate. The organic phase is washed with 1 N HCl, saturated $NaHCO_3$ and brine. After drying over sodium sulfate, the solvent is removed on the rotary evaporator. The residue is taken up in a small amount of toluene and is concentrated again. The product 13a is used as such in the next reaction.

STEP I

(3R, 4R)1,1-DIBROMO-3-t.BUTYL DIMETHYLSILYLOXY-4-METHOXY-4-METHYL-1-OCTEN (4b)

To a solution of tetrabromomethane (2 eq, 98.28 g, 296 mmol) in dry dichloromethane (250 ml), under nitrogen, at 0° C. is added dropwise a solution of $Ph_3P$ (4 eq, 155 g, 592 mmol) in dry dichloromethane (250 ml). The speed of addition is regulated so that the temperature of the reaction stays below 20° C. The solution is orange-red. After 10 min, the cooling bath is removed and the aldehyde 13a in solution in dichloromethane (100 ml) is added dropwise. The mixture is stirred at room temperature for 3 h. The reaction is cooled at −20° C., and triethylamine (4 eq, 88 ml, 636 mmol) is added, followed by the very slow addition of water (300 ml), that gives an exothermic reaction. Precipitation occurs, water (2 L) is added to dissolve the precipitate, then the compound is extracted with dichloromethane (3 L). The organic phase is washed with 1 N HCl, saturated $NaHCO_3$, and brine. After drying over sodium sulfate, the solvent is evaporated. The residue is triturated with petroleum ether to precipitate triphenylphosphine oxide which is filtered off. The solvent is removed under pressure. A second treatment with petroleum ether precipitates a second crop of triphenylphosphine which is filtered again. Finally, the solvent is evaporated and the residue is purified by filtration through a short path of silicagel, eluting with petroleum ether/ethyl acetate (90/10) to yield the desired vinyl dibromide 4b (60 g, 91%).

Step J

(3R,4R)3-t.BUTYL DIMETHYLSILYLOXY-4-METHOXY-4-METHYL-1-OCTYNE (4a)

Magnesium turnings (1.3 eq, 4.2g, 175 mmol) in anhydrous THF (50 ml) are activated with a trace of I2 or CH3I. A solution of the vinyl dibromide 4b (60 g) in anhydrous THF (600 ml) is added at such a rate to maintain a gentle reflux (some heating may be necessary). Stirring is continued at room temperature for 2h. Ethyl ether (2 L) is added, the organic layer is washed with 1 N HCl, saturated NaHCO3 and brine. The solution is dried over sodium sulfate and evaporated. The oil is distilled using a small Vigreux column at 66° C. under 0.01 mmHg to yield the desired product 4a (31.4 g, 81.7%). GC: 94% purity.

EXAMPLE II

Preparation of (3R,4R)3-TETRAHYDROPYRANYLOXY-4-METHOXY-4-METHYL-1-OCTYNE (4a)

STEP A

(2R,3R)1-BENZYLOXY-2-TETRAHYDROPYRANYLOXY-3-METHOXY-3-METHYL-6-HEPTENE (11b)

A solution of (2R,3R)1-benzyloxy-3-methoxy-3-methyl-6-heptene-2-ol (10) (37.1 mmol, 9.8 g), dihydropyran (55.7 mmol, 5.1 ml) and pyridinium paratoluene sulfonate (3.71 mmol, 0.93 g) in anhydrous dichloromethane (100 ml) is stirred under nitrogen atmosphere for 24 h. Ether (400 ml) is added, and the organic layer is washed with water, brine, saturated aqueous NaHCO3 and brine. After drying over anhydrous magnesium sulfate the solvent is flash evaporated. The product 11b is used as such in the next reaction.

STEP B

(2R,3R)2-TETRAHYDROPYRANYLOXY-3-METHOXY-3-METHYL-1-HEPTANOL (12b)

A mixture of (2R,3R)1-benzyloxy-2-tetrahydropyranyloxy-3-methoxy-3-methyl-6-heptene (1.78 mmol, 620 mg) and Pd(OH)2 on carbon (60 mg) in methanol (8 ml) is stirred 3 h under an hydrogen atmosphere whereby 82 ml of hydrogen is absorbed. The catalyst is filtered, washed with methanol and the methanol is removed in vacuo. The alcohol 12b is used as such in the next reaction.

STEP C

(2R,3R)2-TETRAHYDROPYRANYLOXY-3-METHOXY-3-METHYL(HEPTANALDEHYDE (13b)

To a solution of (2R,3R)2-tetrahydropyranyloxy-3-methoxy-3-methyl-1-heptanol (0.89 mmol, 230 mg) and dimethylsulfoxide (1.78 mmol, 0.13 ml) in anhydrous dichloromethane (5 ml) at −78° C. under N2 atmosphere is added dropwise a solution of oxalylchloride (1.16 mmol, 0.1 ml) in dichloromethane (2 ml). The solution is stirred 15 min, and triethylamine (3.56 mmol, 0.5 ml) is added. The mixture is kept 10 min at −78° C., and is then allowed to warm to room temperature. Water (10 ml) and ether (50 ml) are added. The organic layer is separated and washed with HCl 1 N, saturated aqueous NaHCO3 and brine. Drying over anhydrous magnesium sulfate and concentration gives a colorless oil, which is used as such in the next reaction.

STEP D

(3R,4R)1,1-DIBROMO-3-TETRAHYDROPYRANYLOXY-4-METHOXY-4-METHYL-1-OCTENE (14b)

To a solution of CBr4 (1.78 mmol, 0.59g) in dichloromethane (3 ml) at 0° C. is added triphenylphosphine (3.56 mmol, 0.93 g) in dichloromethane (3 ml). The orange-red solution is stirred for 30 min and a solution of 13b (0.89 mmol, crude previous reaction) in dichloromethane is added. After 1 h triethylamine (3.56 mmol, 0.5 ml) is added, followed by the slow addition of water (10 ml) (exothermic). Ether (50 ml) is added, the water layer is removed and the organic layer is washed in brine, dried over anhydrous MgSO4 and concentrated in vacuo. Hexane is added to precipitate the triphenylphosphine oxide, and the mixture is filtered through a short path of silica gel; the filter cake is washed with 30% ether in hexane. The oil obtained after flash evaporation (240 mg, 65%) is used without purification in the reactions to prepare (3R,4R)3-tetrahydropyranyloxy-4-methoxy-4-methyl-1-octyne by U method A or method B.

STEP E

(3R,4R)3-TETRAHYDROPYRANYLOXY-4-METHOXY-4-METHYL-1-OCTYNE (4a)

Method A

A solution of (3R,4R)1,1-dibromo-3-tetrahydropyranyloxy-4-methoxy-4-methyl-1-octene (240 mg; 0.58 mmol) in THF (2 ml) is added dropwise to a refluxing mixture of activated magnesium turnings (activated with I2, 183 mg, 0.75 mmol) in THF (1 ml). The mixture is refluxed for 1 h, hexane (5 ml) is added and the suspension is filtered through a short path of silica gel. The filter cake is washed with ether and the solvent is removed in vacuo. The alkyne (3R,4R)3-tetrahydropyranyloxy-4-methoxy-4-methyl-1-octyne is purified by column chromatography on silica gel, eluting with 5% EtOAc in petroleum ether, to afford (3R,4R)3-tetrahydropyranyloxy-4-methoxy-4-methyl-1-octyne.

Method B

To a solution of (3R,4R)1,1-dibromo-3-tetrahydropyranyloxy-4-methoxy-4-methyl-1-octene in THF (3 ml) under nitrogen atmosphere at −78° C. is added dropwise a solution of n-butyllithium in hexane (0.4 ml, 1.5 M, 0.6 mmol). The reaction is stirred for 1 h at −78° C. and the reaction mixture is allowed to warm to room temperature. After 1 h hexane and water are added, the organic phase is separated and washed with brine, dried over MgSO4 and evaporated. Purification by chromatography gives the desired alkyne.

TWO COMPONENT MICHAEL ADDITION REACTION

EXAMPLE III

Preparation of (84,11R,12R,15,16R)11,15-DIHYDROXY-16-METHYL-16-METHOXY-(9-OXO-PROST-13-EN-1-OIC ACID, METHYL ESTER (1)

Step A t-(3R,4R)3-TETRAHYDROPYRANYLOXY-4-METHOXY-4-METHYL-1-TRIBUTYL-STANNYL-1-OCTENE (4c)

A mixture of (3R,4R)3-tetrahydropyranyloxy-4-methoxy-4-methyl-l-octyne (2.54 g, 10 mmol), Bu3SnH (3.23 ml, 12 mmol) and AIBN (10 mg) is heated under nitrogen atmosphere at 130° C. during 30 min. AIBN (10 mg) is added again, and the heating is continued for 30 min. The product (3R,4R)3-tetrahydropyranyloxy-4-methoxy-4-methyl-1-tributylstannyl-l-octene is purified by column chromatography on silica gel, eluting with 5% EtOAc in petroleum ether. 4.88 g (89%) of t(3R,4R)3-tetrahydropyranyloxy-4-methoxy-4-methyl-1-tributylstannyl -1-octene (4c) is obtained.

Step B (R)4-TETRAHYDROPYRANYLOXY-2-(6-CARBOMETHOXYHEXYL)-CYCLOPENTEN-2-ENONE (5)

A solution of (R)4-hydroxy-2-(6-carbomethoxyhexyl)-cyclopenten-2-enone (2.4 g, 10 mmol), dihydropyran (137 ml, 15 mmol) and pyridinium p.toluenesulfonate (250 mg, 1 mmol) in anhydrous $CH_2Cl_2$ (20 ml) is stirred for 3 h at room temperature. Ether (200 ml) is added, and the organic phase is washed with water and brine. After drying over $MgSO_4$ the solvent is removed in vacuo to afford 3.18 g (98%) of (R)4-tetrahydropyranyloxy-2-(6-carbomethoxyhexyl)-cyclopenten-2-enone (18). The product is used with purification in the next reaction.

Step C (8R,11R,12R,15R,16R)11,15-DITETRAHYDROPYRANYLOXY-16-METHYL-16-METHOXY-9-OXO-PROST -13-EN-1-OIC ACID, METHYL ESTER (6)

Thiophene (13 mmol, 1.04 ml) in THF (10 ml) at −78° C.C is treated with n-buthyllithium in hexane (13 mmol, 1.5 M, 8.66 ml). The solution is stirred for 15 min at −78° C., whereafter the temperature is raised to −20° C. for 30 min. The mixture is transferred to a slurry of CuCN (13 mmol, 1.16 g) in THF (10 ml) at −78° C., and the flask is rinsed with THF (10 ml). Warming to −40° C. gives a brown, homogenous solution. In a second flask, t(3R,4R)3-tetrahydropyranyloxy-4-methoxy-4-methyl-1-tributylstannyl-1-octene (9 mmol, 4.88 g) in THF (10 ml) at −78° C. is treated with n-butyllithium in hexane (9 mmol, 1.5 M, 6.0 ml). The mixture is stirred for 10 min at −78° C., and the above-prepared solution of ThCuCNLi in THF is added. The solution is stirred at −78° C. for 30 and a solution of (R)4-tetrahydropyranyloxy-2-(6-carbomethoxyhexyl)-cyclopenten-2-enone (3.1 g, 9 mmol) in THF (10 ml) is added dropwise. The mixture is stirred for 30 min at −78° C. followed by 15 min at −50° C. and is then quenched with 10% NH4OH saturated in NH4Cl saturated (50 ml). The suspension is allowed to warm to room temperature, affording a dark blue aqueous layer. The organic layer is diluted with petroleum ether, the water layer is removed and the organic layer is washed with brine, dried over magnesium sulfate and concentrated in vacuo. The obtained material is subjected without purification to the hydrolysis procedure of Step D.

Step D (8R,11R,12R,15R,16R)11,15-DIHYRDOXY-16-METHYL-16-METHOXY-9-OXO-PROST-13-EN-1-OIC ACID, METHYL ESTER (1)

A solution of the crude bis tetrahydropyranyl ether of Step C in formic acid, (16 ml), $H_2O$ (30 ml) and THF (35 ml) is stirred for 24 h at room temperature. The mixture is cooled in an ice-water bath, $H_2O$ (30 ml) is added, and solid NaHCO3 is added till a pH of 7 is reached. The aqueous layer is extracted with ether, the combined organic layers are washed with saturated NaHCO3 and brine, dried over MgSO4 and concentrated in vacuo. Column chromatograph separation on silica gel, eluting with 2% MeOH in AcOEt, gives (8R,11R,12R,15R,16R)-11,15-dihydroxy-16-methyl-16-methoxy-9-oxo-prost-13-en-1-oic acid, methyl ester· which solidifies in the freezer (m.p. 44–45° C.).

ALTERNATE PROCEDURE FOR TWO COMPONENT MICHAEL ADDITION REACTION

EXAMPLE IV

Preparation of (8R,11R,12R,15R,16R)11,15-DI-t.BUTYLDIMETHYLSILYLOXY-16-METHYL-16-METHOXY-9-OXO-PROST-13-EN-1-OIC ACID, METHYL ESTER (6)

Step A (3R,4R)3-t.BUTYLDIMETHYLSILYLOXY-4-METHOXY-4-METHYL-1-TRIBUTYL-STANNYL-1-OCTENE (4c)

A mixture of (3R,4R)3-t.butyldimethylsilyloxy-4-methoxy-4-methyl-l-octyne (1) (5.7 g, 20 mmol) and tri-n-butylstannylhydride (8.7 g, 30 mmol) and 40 mg of azoisobutyronitrile is heated to 2 hr to about 130° C. (oil bath temperature). The mixture is allowed to cool to room temperature and filtered through a pad of silica gel. Elution with n-hexane removes impurities ($R_f$=0.8); (3R,4R)3-t.butyldimethylsilyloxy-4-methoxy-4-methyl-1-tributylstannyl-l-octene being eluted with a mixture of ether/hexane: 1/5. Final purification of the (3R,4R)3-t.butyldimethylsilyloxy-4-methoxy-4-methyl-1-tributyl-stannyl-1-octene is achieved through chromatography (silica gel, eluant: hexane) to afford 8.1 g (70%) of tin olefine.

Step B (3R)3-t.BUTYLDIMETHYLSILYLOXY-5-OXO-1-CYCLOPENTENEHEPTANOIC-ACID, METHYL ESTER (5)

A solution of (3R)3-hydroxy-5-oxo-l-cyclopenteneheptanoic acid, methyl ester (1.34 g, 5.6 mmol), t.butyl dimethylsilyl chloride (1.69 g, 11.2 mmol), and imidazole (0.8 g, 11.2 mmol) in DMF (11.2 ml) is stirred at room temperature for 30 min under $N_2$ atmosphere. Petroleum ether (100 ml) is added, and the organic layer washed with H2), 1 N HCl, brine, concentrated aqueous NaHCO3, and again with brine (each 10 ml). After drying (MgSO4) the solvents are removed on the rotary evaporator (20 Torr, 30° C.) to afford quantitatively (3R)3-t.butyldimethylsilyloxy-5-oxo-l-cyclopenteneheptanoic acid, methyl ester.

Step C (8R,11R,12R,15R,16R)11,15-DI-t.BUTYLDIMETHYLSILYLOXY-16-METHYL-16-METHOXY-9-OXO-PROST -13-EN-1-OIC ACID, METHYL ESTER (6)

A solution of (3R,4R)3-t.butyldimethylsilyloxy-4-methoxy-4-methyl-l-tributylstannyl-l-octene 2 (0.58 g, 1 mmol) in THF (1 ml) was treated at −78° C. under nitrogen with n-butyllithium (0.65 ml, 1.6 M in hexane), stirred for 10 min at −78° C. and a solution of copper (I) iodide (0.19 g, 1 mmol) and tri-n-butyl phosphine (0.65 ml, 2.6 mmol) in 1 ml of THF was added. The reaction mixture was warmed to −40° C. and stirred for 1 h when a solution of the (3R)3-t.butyldimethylsilyloxy-5-oxo-l-cyclopenteneheptanoic acid, methyl ester (0.35 g, 1 mmol) in THF (1 ml) was added. The mixture was stirred at −40° C. for 1 h before acetic acid (0.1 ml) was added. The mixture was allowed to warm to room temperature, diluted with 100 ml of hexane, washed with water, NaHCO3 saturated, and brine and then dried over MgSO4. Solvents were flash-evaporated (20 Torr, 30° C.) and the oily residue purified by chromatography on silica gel 25 g, 230–400 mesh, eluant: petroleum ether (100 ml), then petroleum ether/EtOAc: 95/5 (200 ml), then petroleum ether/EtOAc: 92/8. The product containing fractions were combined and solvents removed in vacuo to afford 0.13 g of pure (8R,11R,12R,15R,16R)-11,15-di-t.butyldimethylsilyloxy-16-methoxy-9-oxo-prost-13-en-1-oic acid, methyl ester.

THREE COMPONENT CONDENSATION REACTION

EXAMPLE V (8R,11R,12R,15R,16R)11,15-DIHYDROXY-16-METHYL-16-METHOXY-9-OXO-PROST-13-EN-1 3-EN-1-OIC ACID, METHYL ESTER (1)

Step A (8R,11R,12R,15R,16R)11,15-DI-t.BUTYL DIMETHYLSILYLOXY-7-HYDROXY-16-METHYL-16-METHOXY -9-OXO-PROST-13-EN-1-OIC ACID, METHYL ESTER (14)

To a nitrogen-blanketed solution of -t(3R,4R)3-t.butyl-dimethylsilyloxy-4-methoxy-l-tributylstannyl-4-methyl -1-octene (0.50 g, 0.87 mmol) in 2 ml of THF at −78° C. was added n-butyl-lithium (0.55 ml, 1.6 M in hexane) and stirring was continued for 10 min, before a precooled (−78° C.) solution of CuI (0.17 g) and nBu3P (0.46 g) in THF (2 ml) was added. The mixture was allowed to warm to −35° C. during 5 min, cooled again to −78° C. and stirred for 1 h. A solution of (4R)4-t.butyldimethylsilyl-oxo-2-cyclopentene-1-one (0.19 g) in 1 ml THF was added, and the mixture allowed to warm to −40° C. during 1 hr. After stirring at −40° C. for 5 min, the reaction mixture was cooled again to −78° C. and methyl 7-oxo-heptanoate (0.17 g) dissolved in 0.5 ml of THF was added. Stirring was continued for 10 min at −78° C. before AcOH (0.08 g) was added. The mixture was allowed to warm up to room temperature, poured into Et2O (100 ml) and water (100 ml) was added. The layers were separated, the aqueous layer extracted again with Et2O (100 ml) and the combined organic layers washed with water (2×100 ml) and then brine (100 ml). The organic layer was dried (MgSO4 ) and flash evaporated (20 Torr) to afford crude product; rapid filtration through a SiO2 pad facilitates removal of nonpolar impurities (eluant Et2O/hexane: 1/5) to obtain (8R,11R,12R,15R,16R)11,14-di-t.butyldimethylsilyloxy-7-hydroxy-16-methyl-16-methoxy-9 -oxo-prost-13-en-1-oic acid, methyl ester (14) (eluant Et2O/hexane: 2–1/1) used as such in the next step.

Step B (8R,11R,12R,15R,16R)11,15-DI-t.BUTYLDIMETHYLSILYLOXY-16-METHYL-16-METHOXY-9-OXO-PROST -7,13-DIEN-1-OIC ACID METHYL ESTER (15)

To a solution of (8R,11R,12R,15R,16R)11,15-di-t.butyl-dimethylsilyloxy-7-hydroxy-16-methyl-16-methoxy-9-oxo-prost-13-en-l-oic acid, methyl ester (0.21 g, 0.32 mmol) in CH2Cl2 (1.6 ml) was added MsCl (0.1 g) and 4-alminodimethylpyridine (0.2 g). The mixture was stirred for 40 min, poured into CH2Cl2 (100 ml) and water was added (100 ml). The layers were separated, the aqueous layer extracted again with CH2Cl2 (100 ml) and the combined aqueous layers were washed with water (2×100 ml) and brine (50 ml). The organic layer was dried (MgSO4) and flash evaporated to afford crude (8R,11R,12R,15R,16R) 11,15-di-t.butyl-dimethylsilyloxy-16-methyl-16-methoxy-9-oxo-prost-7,13-dien-l-oic acid, methyl ester purified by silicagel chromatography (30 g SiO2, 230–400 mesh, eluant Et2O/hexane 1:5) to obtain pure (8R,11R,12R,15R,16R)11,15-di-t.butyl-dimethylsilyloxy-16-methyl-16-methoxy-9 -oxo-prost-7,13-dien-l-oic acid, methyl ester.

Step C (8R,11R,12R,15R,16R)11,15-DI-t.BUTYLDIMETHYLSILYLOXY-16-METHYL-16-METHOXY-9-OXO-PROST ESTER (16)

A mixture of (8R,11R,12R,15R,16R)11,15-Di-t.butyl-dimethylsilyloxy-16-methyl-16-methoxy-9-oxo-prost7,13-en-1-oic acid, methyl ester (0.09 g, 0.14 mmol), 0.205 g tri-n-butylstannylhydride and 2 mg of t.butyl peroxide was heated for 15 min to 110° C. (oil bath temperature). The reaction mixture was allowed to cool to room temperature and then chromatographed on silica gel (10 g, 230–400 mesh, eluant: Et2O/hexane: 1/5) to give the protected prostaglandin derivative (11R,12R,15R,16R)11,15-di-t.butyldimethylsilyloxy-16-methyl-16-methoxy-9-oxo-prost-13-en -1-oic acid, methyl ester.

Step D (8R,11R,12R,15R,16R)11,15-DIHYDROXY-16-METHYL-16-METHOXY-9-OXO-PROST-13-EN-1-OI C ACID, METHYL ESTER (1)

A mixture of (8R,11R,12R,15R,16R)11,15-di-t.butyl-dimethylsilyloxy-16-methyl-16-methoxy-9 -oxo-prost-13-en-1-oic acid, methyl ester (0.045 g, 0.07 mmol) in 0.5 ml of HOAc/H2O)/THF: 3/1/1) was stirred for 48 h at room temperature. After adding more water (5 ml), the mixture was neutralized by addition of an aqueous solution of Na2HPO4, and extracted with Et2O (2×10 ml). The combined organic layers were washed with aqueous NaHCO3, water and then brine, dried (MgSO4) and flash evaporated to afford crude (8R,11R,12R,15R,16R)11,15-Dihydroxy-16-methyl-16-methoxy-9-oxo-prost-13-en-1-oic acid, methyl ester. Final purification was achieved by chromatography on 10 g of silicagel (eluant EtOAc).

ALTERNATE PROCEDURE FOR TWO COMPONENT MICHAEL ADDITION

EXAMPLE VI

Preparation of (8R,11R,12R,15R,16R)11,15-DIHYDROXY-16-METHYL-16-METHOXY-9-OXO-PROST-3-EN-1-OIC ACID, METHYL ESTER (1)

Step A (R)4-TERT-BUTYLDIMETHYLSILYLOXY-2-(6-CARBOMETHOXYHEXYL)-CYCLOPENT-2-ENONE (5)

A solution of (R)4-hydroxy-2-(6-carbomethoxyhexyl)-cyclopent-2-enone (1.34 g; 5.58 mmol), t. butyl dimethylsilyl chloride (1.69 g; 11.2 mmol) and imidazole (0.8 g, 11.7 mmol) in dimethylformamide (11.2 ml) is stirred under nitrogen atmosphere for 30 minutes. The reaction mixture is diluted with petroleum ether, and the organic layer is washed with 1N HCl, water, saturated aqueous NaHCO3 and brine. The solvent is evaporated in vacuo. Column chromatographic purification on silica gel, eluting with 5% EtOAc in petroleum ether, gives 1.88 g (95%) or (R)4-t.-butyldimethylsilyloxy-2-(5-carbomethoxyhexyl)-cyclopent-2-enone.

Step B 11R,12R,15R,16R)11,15-DI-TERT-BUTYLDIMETHYLSILYLOXY-(16-METHYL-16-METHOXY-9-OXO-PROST-13-EN-1-OIC ACID, METHYL ESTER (6)

To a solution of (3R,4R)3-t.butyldimethylsilyloxy-1-tributylstannyl-4-methoxy-4-methyl-1-octene (471 mg, 0.82 mmol) in tetrahydrofuran (1 ml) at −78° C. under nitrogen atmosphere is added n-BuLi (0.55 ml, 0.82 mmol; 1.5 M in hexane). The solution is stirred for 15 minutes at −78° C. and a solution of (R)4-t.butyldimethylsilyloxy-2-(6-carbomethoxyhexyl)-2-cyclopentenone (267 mg, 0.75 mmol) in tetrahydrofuran (2 ml) is added. The mixture is stirred for 30 minutes at −78° C. and the reaction is quenched with 10 ml of a 10% saturated NH4OH in saturated NH4Cl solution. The cooling bath is removed, and the mixture is allowed to warm to room temperature. The organic layer is diluted with petroleum ether (50 ml), the blue aqueous layer is removed and the organic layer is washed with brine and dried over MgSO4. Column chromatographic purification, eluting with 5% EtOAc in petroleum ether yields the desired bis-t.butyl dimethylsilyl ether.

Step C (8R,11R,12R,15R,16R)11,15-DIHYDROXY-16-METHYL-16-METHOXY-9-OXO-PROST-13-EN-1-OIC ACID, METHYL ESTER (1)

A solution of the bis t.butyldimethylsilyl ether of Step B (45 mg, 0.07 mmol) in HOAc/H2O/tetrahydrofuran:
(3/1/1) (0.5 ml) is stirred for 48 h at room temperature. Water (5 ml) is added, and the mixture is neutralized with solid potassium carbonate. The aqueous layer is extracted with ether, the combined organic layers are washed with brine, dried over MgSO4 and concentrated in vacuo. Column chromatography (2% methanol in EtOAc) on silica gel gives the desired product.

We claim:

1. Compound of the formulae:

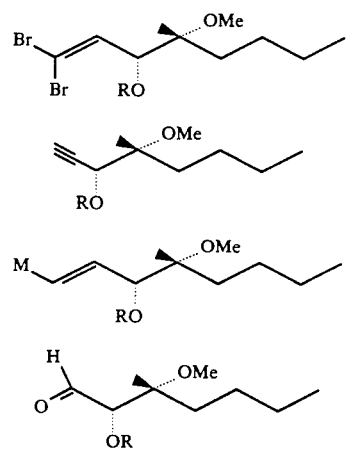

wherein M is (Bu)3Sn-, Li, a cupric complex or an organocuprate complex, and R is THP or TBS.

2. A compound according to claim 1 which can be described by the formula:

3. A compound according to claim 1 which can be described by the formula:

4. A compound according to claim 1 which can be described by the formula:

5. A compound according to claim 1 which can be described by the formula:

* * * * *